(12) United States Patent
Burrell et al.

(10) Patent No.: US 6,723,350 B2
(45) Date of Patent: Apr. 20, 2004

(54) LUBRICIOUS COATINGS FOR SUBSTRATES

(75) Inventors: Robert Edward Burrell, Sherwood Park (CA); Hua Qing Yin, Sherwood Park (CA); Antony George Naylor, Sherwood Park (CA); Peter Howard Moxham, Sherwood Park (CA); Walter Carlton Theodore Cholowski, Edmonton (CA); Leonard Salvin Bowlby, Sherwood Park (CA); David James Field, Edmonton (CA)

(73) Assignee: Nucryst Pharmaceuticals Corp., Alberta (CA)

( * ) Notice: Subject to any disclaimer, the term of this patent is extended or adjusted under 35 U.S.C. 154(b) by 152 days.

(21) Appl. No.: 10/131,513

(22) Filed: Apr. 23, 2002

(65) Prior Publication Data

US 2002/0182265 A1 Dec. 5, 2002

Related U.S. Application Data

(63) Continuation-in-part of application No. 09/840,637, filed on Apr. 23, 2001.
(60) Provisional application No. 60/285,884, filed on Apr. 23, 2001.

(51) Int. Cl.[7] .................. A61K 9/00; A61K 33/38; A01N 59/16; C23C 14/06; C23C 14/14

(52) U.S. Cl. .............. 424/618; 424/405; 424/489; 424/600; 424/604; 424/617; 424/620; 424/630; 424/639; 424/641; 424/646; 424/649; 424/650; 424/651; 424/652; 424/653; 424/654; 424/655; 424/682; 427/250; 106/1.05; 106/1.13; 106/1.14; 106/1.15; 106/1.18; 106/1.19; 106/1.21; 148/513; 148/537; 148/559; 148/678; 148/679; 514/951

(58) Field of Search ............... 424/405, 489, 424/600, 604, 617, 618, 620, 630, 639, 641, 646, 649, 650, 651–655, 682; 427/250; 106/1.05, 1.13, 1.14, 1.15, 1.18, 1.19, 1.21; 148/513, 537, 559, 678, 679; 514/951

(56) References Cited

U.S. PATENT DOCUMENTS

| | | | |
|---|---|---|---|
| 3,757,786 A | 9/1973 | Smith | 606/224 |
| 3,800,792 A | 4/1974 | McKnight et al. | 602/50 |
| 3,918,446 A | 11/1975 | Buttaravoli | 604/180 |
| 4,059,105 A | 11/1977 | Citruzzula et al. | 604/180 |
| 4,324,237 A | 4/1982 | Buttaravoli | 602/54 |
| 4,355,636 A | 10/1982 | Oetjen et al. | 128/204.13 |
| 4,476,590 A | 10/1984 | Scales et al. | 623/23.57 |
| 4,581,028 A | 4/1986 | Fox, Jr. et al. | 623/2.42 |
| 4,596,556 A | 6/1986 | Morrow et al. | 604/70 |
| 4,633,863 A | 1/1987 | Filips et al. | 128/165 |
| 4,749,572 A | 6/1988 | Ahari | 424/618 |
| 4,790,824 A | 12/1988 | Morrow et al. | 604/143 |
| 4,803,066 A | 2/1989 | Edwards | 514/184 |
| 4,828,832 A | 5/1989 | De Cuellar et al. | 424/618 |
| 4,847,049 A | 7/1989 | Yamamoto | 422/24 |
| 4,952,411 A | 8/1990 | Fox, Jr. et al. | 424/618 |
| 4,960,413 A | 10/1990 | Sagar et al. | 604/289 |
| 5,019,096 A | 5/1991 | Fox, Jr. et al. | 623/1 |
| 5,064,413 A | 11/1991 | McKinnon et al. | 604/70 |
| 5,122,418 A | 6/1992 | Nakane et al. | 424/401 |
| 5,143,717 A | 9/1992 | Davis | 424/45 |
| 5,236,421 A | 8/1993 | Becher | 604/180 |
| 5,270,358 A | 12/1993 | Asmus | 524/55 |
| 5,312,335 A | 5/1994 | McKinnon et al. | 604/72 |
| D349,958 S | 8/1994 | Hollis et al. | D24/112 |
| 5,369,155 A | 11/1994 | Asmus | 524/55 |
| 5,372,589 A | 12/1994 | Davis | 604/180 |
| 5,383,851 A | 1/1995 | McKinnon, Jr. et al. | 604/68 |
| 5,399,163 A | 3/1995 | Peterson et al. | 604/68 |
| 5,454,886 A | 10/1995 | Burrell et al. | 148/565 |
| 5,454,889 A | 10/1995 | McNicol et al. | 149/7 |
| 5,457,015 A | 10/1995 | Boston | 430/529 |
| 5,520,639 A | 5/1996 | Peterson et al. | 604/68 |
| 5,534,288 A | 7/1996 | Gruskin et al. | 427/2.31 |
| 5,563,132 A | 10/1996 | Bodaness | 514/185 |
| 5,569,207 A | 10/1996 | Gisselberg et al. | 604/175 |

(List continued on next page.)

FOREIGN PATENT DOCUMENTS

| | | | |
|---|---|---|---|
| CA | 2242033 | 1/1999 | |
| CN | 1082645 | 2/1994 | |
| CN | 1241662 | 1/2000 | D06M/11/83 |
| CN | 1262093 | 8/2000 | |
| CN | 1279222 | 1/2001 | C04B/41/85 |
| CN | 1291666 | 4/2001 | D06M/11/58 |

(List continued on next page.)

OTHER PUBLICATIONS

Burrell, et al. "Efficacy of Silver–Coated Dressings as Bacterial Barriers in a Rodent Burn Sepsis Model" *Wounds* 1999; 11(4): 64–71.

Demling, et al., "The Role of Silver in Wound Healing: Effects of Silver on Wound Management," *Wounds*, vol. 13, No. 1, Jan./Feb. 2001 Supplement A; pp. 5–14.

(List continued on next page.)

*Primary Examiner*—John Pak
(74) *Attorney, Agent, or Firm*—Fish & Richardson P.C.

(57) ABSTRACT

The invention provides methods and kits to form water swellable gel coatings, preferably lubricious coatings, on substrates, and coated substrates thus formed. The coatings contain one or more antimicrobial metals formed with atomic disorder, together with one or more antimicrobial metals formed with atomic disorder such that the coatings provide an antimicrobial and anti-inflammatory effect when wet. The invention also provides a method to produce metal powders by sputtering a coating onto a moving surface, and then scraping the coating with one or more scrapers to produce the metal powder. The method is particularly useful for producing large amounts of nanocrystalline antimicrobial metal powders formed with atomic disorder, useful in the water swellable gel coatings of this invention.

4 Claims, No Drawings

U.S. PATENT DOCUMENTS

| | | | |
|---|---|---|---|
| 5,578,073 A | 11/1996 | Haimovich et al. | 623/1.48 |
| 5,631,066 A | 5/1997 | O'Brien | 428/195.1 |
| 5,681,575 A | 10/1997 | Burrell et al. | 424/423 |
| 5,744,151 A | 4/1998 | Capelli | 424/405 |
| 5,753,251 A | 5/1998 | Burrell et al. | 424/426 |
| 5,770,255 A | 6/1998 | Burrell et al. | 427/2.1 |
| 5,770,258 A | 6/1998 | Takizawa | 427/64 |
| 5,792,793 A | 8/1998 | Oda et al. | 514/495 |
| 5,837,275 A | 11/1998 | Burrell et al. | 424/409 |
| 5,848,995 A | 12/1998 | Walder | 604/265 |
| 5,895,419 A | 4/1999 | Tweden et al. | 623/2.36 |
| 5,899,880 A | 5/1999 | Bellhouse et al. | 604/70 |
| 5,945,032 A | 8/1999 | Breitenbach et al. | 252/186.29 |
| 5,958,440 A | 9/1999 | Burrell et al. | 424/423 |
| 5,981,822 A | 11/1999 | Addison | 602/41 |
| 5,985,308 A | 11/1999 | Burrell et al. | 424/426 |
| 6,010,478 A | 1/2000 | Bellhouse et al. | 604/70 |
| 6,013,050 A | 1/2000 | Bellhouse et al. | 604/70 |
| 6,017,553 A | 1/2000 | Burrell et al. | 424/411 |
| 6,022,547 A | 2/2000 | Herb et al. | 424/401 |
| 6,071,541 A | 6/2000 | Murad | 424/616 |
| 6,071,543 A | 6/2000 | Thornfeldt | 424/642 |
| 6,096,002 A | 8/2000 | Landau | 604/68 |
| 6,123,925 A | 9/2000 | Barry et al. | 424/49 |
| 6,126,931 A | 10/2000 | Sawan et al. | 424/78.09 |
| 6,165,440 A | 12/2000 | Esenaliev | 424/1.11 |
| 6,187,290 B1 | 2/2001 | Gilchrist et al. | 424/45 |
| 6,197,351 B1 | 3/2001 | Neuwirth | 424/618 |
| 6,201,164 B1 | 3/2001 | Wulff et al. | 602/48 |
| 6,224,898 B1 | 5/2001 | Balogh et al. | 424/445 |
| 6,238,686 B1 | 5/2001 | Burrell et al. | 424/423 |
| 6,258,385 B1 | 7/2001 | Antelman | 424/618 |
| 6,277,169 B1 | 8/2001 | Hampden-Smith et al. | 75/336 |
| 6,294,186 B1 | 9/2001 | Beerse et al. | 424/405 |
| 6,312,643 B1 * | 11/2001 | Upadhya et al. | 419/33 |
| 6,333,093 B1 | 12/2001 | Burrell et al. | 428/194 |
| 6,365,130 B1 | 4/2002 | Barry et al. | 424/405 |
| 6,544,357 B1 * | 4/2003 | Hehmann et al. | 148/20 |
| 2001/0010016 A1 | 7/2001 | Modak et al. | 623/1.42 |
| 2002/0001628 A1 | 1/2002 | Ito | 424/618 |
| 2002/0014406 A1 * | 2/2002 | Takashima | 204/298.13 |
| 2002/0016585 A1 | 2/2002 | Sachse | 604/544 |
| 2002/0025344 A1 | 2/2002 | Newman et al. | 424/618 |
| 2002/0045049 A1 | 4/2002 | Madsen | 428/423.3 |
| 2002/0051824 A1 | 5/2002 | Burrell et al. | 424/618 |
| 2002/0192298 A1 | 12/2002 | Burrell et al. | 424/618 |

FOREIGN PATENT DOCUMENTS

| | | | | |
|---|---|---|---|---|
| CN | 1291667 | 4/2001 | | D06M/13/144 |
| CN | 1306117 | 8/2001 | | D06M/11/58 |
| CN | 1322474 | 11/2001 | | A01N/59/16 |
| CN | 1322874 | 11/2001 | | D06M/11/83 |
| CN | 1328819 | 1/2002 | | A61K/9/70 |
| CN | 1328827 | 1/2002 | | A61K/33/38 |
| DE | 2748882 | 5/1979 | | |
| DE | 3807944 | 9/1989 | | |
| DE | 195 41 735 A1 | 5/1997 | | |
| EP | 0 081 599 | 6/1983 | | |
| EP | 0 136 768 | 4/1985 | | |
| EP | 62185807 | 8/1987 | | |
| EP | 0 254 413 | 1/1988 | | |
| EP | 0 356 060 | 8/1989 | | |
| EP | 0 355 009 | 2/1990 | | |
| EP | 0 378 147 | 7/1990 | | |
| EP | 0 599 188 | 6/1994 | | |
| EP | 0681841 | 11/1995 | | |
| EP | 0 681 841 A1 | 11/1995 | | |
| EP | 0780138 | 6/1997 | | |
| EP | 0 328 421 A2 | 8/1999 | | |
| EP | 1 159 972 | 12/2001 | | |
| GB | 420052 | 11/1934 | | |
| GB | 427106 | 4/1935 | | |
| GB | 965010 | 7/1964 | | |
| GB | 1270410 | 4/1972 | | |
| GB | 2 073 024 | 10/1981 | | |
| GB | 2 140 684 | 12/1984 | | |
| HU | 980078 A | 9/1999 | | |
| IT | 022309 | 12/1990 | | |
| JP | 60-21912 | 2/1985 | | |
| JP | Sho 58-126910 | 2/1985 | | |
| JP | 04244029 A | 9/1992 | | |
| JP | 11060493 | 3/1999 | | |
| JP | 11 060493 A | 3/1999 | | |
| JP | 11116488 | 4/1999 | | |
| JP | 11 116488 A | 4/1999 | | |
| JP | 11124335 | 5/1999 | | |
| JP | 11 124335 | 5/1999 | | |
| JP | 2000 327578 A | 11/2000 | | |
| JP | 2000327578 | 11/2000 | | |
| WO | 87/07251 | 12/1987 | | |
| WO | WO 89/09054 | 10/1989 | | |
| WO | 92/13491 | 8/1992 | | |
| WO | 93/23092 | 11/1993 | | |
| WO | WO 93/23092 | 11/1993 | | A61L/29/00 |
| WO | 95/13704 | 5/1995 | | |
| WO | WO 95/13704 | 5/1995 | | A01N/59/16 |
| WO | WO 96/17595 | 6/1996 | | |
| WO | 98/41095 | 9/1998 | | |
| WO | WO 98/41095 | 9/1998 | | A01N/59/00 |
| WO | 98/51273 | 11/1998 | | |
| WO | 00/24946 | 5/2000 | | |
| WO | WO 00/27390 | 5/2000 | | |
| WO | 00/27390 | 5/2000 | | |
| WO | WO 00/30697 | 6/2000 | | A61L/29/10 |
| WO | WO 00/44414 | 8/2000 | | A61L/27/50 |
| WO | WO 00/64505 | 11/2000 | | A61L/27/02 |
| WO | WO 00/64506 | 11/2000 | | A61L/31/02 |
| WO | WO 00/78281 | 12/2000 | | A61K/7/48 |
| WO | WO 00/78282 | 12/2000 | | A61K/7/48 |
| WO | 01/15710 | 3/2001 | | |
| WO | WO 01/24839 | 4/2001 | | A61L/15/22 |
| WO | WO 01/26627 | 4/2001 | | |
| WO | WO 01/27365 | 4/2001 | | D01H/4/28 |
| WO | WO 01/34686 | 5/2001 | | C08J/9/00 |
| WO | WO 01/41774 | 6/2001 | | A61K/31/78 |
| WO | WO 01/41819 | 6/2001 | | A61L/15/28 |
| WO | 01/43788 | 6/2001 | | |
| WO | 01/49115 | 7/2001 | | |
| WO | 01/49301 | 7/2001 | | |
| WO | WO 01/49301 | 7/2001 | | |
| WO | 01/49302 | 7/2001 | | |
| WO | WO 01/49303 A1 | 7/2001 | | |
| WO | 01/68179 A1 | 9/2001 | | |
| WO | 01/70052 | 9/2001 | | |
| WO | WO 01/74300 | 10/2001 | | A61K/6/00 |
| WO | 01/80920 | 11/2001 | | |
| WO | 02/09729 | 2/2002 | | |
| WO | WO 02/09729 A2 | 2/2002 | | |
| WO | WO 02/15698 | 2/2002 | | A01N/59/16 |
| WO | WO 02/18003 | 3/2002 | | A61M/25/00 |
| WO | WO 02/18699 | 3/2002 | | D06M/11/83 |
| WO | 02/44625 | 6/2002 | | |

OTHER PUBLICATIONS

Djokic et al., "An Electrochemical Analysis of Thin Silver Films Produced by Reactive Sputtering", *Journal of The Electrochemical Society*, 148 (3) C191–C196 (2001).

Kirsner et al., "The Role of Silver in Wound Healing Part 3: Matrix Metalloproteinsases in Normal and Impaired Wound Healing: A Potential Role of Nanocrystalline Silver", *Wounds* vol. 13, No. 3. May/Jun. 2001, Supplement C, pp. 5–11.

Olson et al., "Healing of Porcine Donor sites Covered with Silver–coated Dressings"* *Eur J Surg* 2000; 166: 486–489.

Ovington, "The Role of Silver in Wound Healing: Why is Nanocrystalline Silver Superior? Nanocrystalline Silver: Where the Old and Familiar Meets a New Frontier," *Wounds*, vol. 13, No. 2, Mar./Apr. 2001, Supplement B; pp. 5–10.

Sant et al., "Novel duplex antimicrobial silver films deposited by magnetron sputtering", *Philosophical Magazine Letters*, 2000, vol. 80, No. 4, 249–256.

Tredget , "Evaluation of Wound Healing using Silver Dressing", Feb. 22, 1996.

Tredget et al., "A Matched–Pair, Randomized Study Evaluating the Efficacy and Safety of Acticoat* Silver–Coated Dressing for the Treatment of Burn Wounds," *Journal of Burn Care & Rehabilitation* Nov./Dec. 1998; 19:531–7.

Voigt, et al., "The Use of Acticoat as Silver Impregnated Telfa Dressings in a Regional Burn and Wound Care Center: The Clinicians View," *Wounds*, vol. 13, No. 2, Mar./Apr. 2001, Supplement B; pp. 11–20.

Wright et al., "Early healing events in a porcine model of contaminated wounds: effects of nanocrystalline silver on matrix metalloproteinases, cell apoptosis, and healing" *Wound Repair and Regeneration* 2002; 10:141–151.

Wright, et al., "The Comparative Efficacy of Two Antimicrobial Barrier Dressings: In–vitro Examination of Two Controlled Release of Silver Dressings" *Wounds* vol. 10, No. 6 Nov./Dec. 1998, pp. 179–188.

Wright, et al., "Efficacy of topical silver against fungal burn wound pathogens", *AJIC* vol. 27, No. 4, Aug. 1999.

Wright, et al., "Wound Management in an era of increasing bacterial antibiotic resistance: A role for topical silver treatment," *AJIC* vol. 26, No. 6; pp. 572–577 Dec. 1998.

JP 2000 327578 A Nov. 28, 2000 (abstract only).
JP 2000 327578 A Nov. 28, 2000 (full document).
JP 11 124335 A May 11, 1999 (abstract only).
JP 11 124335 A May 11, 1999 (full document).
JP 11 116488 A Apr. 27, 1999 (abstract only).
JP 11 116488 A Apr. 27, 1999 (full document).
DE 195 41 735 A1 May 15, 1997 (full document).

Yin et al., "Comparative Evaluation of the Antimicrobial Activity of ACTICOAT* Antimicrobial Barrier Dressing" *Journal of Burn Care & Rehabilitation*, vol. 20, No. 3 May/Jun. 1999.

Yin, et al., "Effect of Acticoat Antimicrobial Barrier Dressing on Wound Healing and Graft Take", *Burn Care & Rehabilitation*, part 2 Jan./Feb. 1999.

Shigemasa et al., "Applications of Chitin and Chitosan for Biomaterials" *Biotechnology & Genetic Engineering Reviews* vol. 13 (14) pp. 383–420, Date Unknown.

Thornton, "Deposition Technologies for Films and Coatings: Coating Deposition by Sputtering" *Materials Science Series* 5 pp. 170–243, 1982.

Sant et al., "Morphology of Novel Antimicrobial Silver Films Deposited By Magnetron Sputtering" *Scripta Materiala*, vol. 41, No. 12, pp. 1333–1339, Nov. 19, 1999.

Merle E. Olson et al "Healing of Porcine Donor Sites Covered with Silver–Coated Dressings", Eur J Surg, 2000; 166: 486–489.

John A. Thornton "Influence of Apparatus Geometry and Deposition Conditions on the Structure and Topography of Thick Sputtered Coatings", J. Vac. Sci, Technol. Vol 11, No. 4 Jul./Aug., 1974 pp. 666–670.

* cited by examiner

LUBRICIOUS COATINGS FOR SUBSTRATES

CROSS-REFERENCE TO RELATED APPLICATIONS

This application is a Continuation-in-part of co-pending U.S. patent application Ser. No. 09/840,637 filed Apr. 23, 2001. This application also claims priority from U.S. Provisional Patent Application No. 60/285,884, filed Apr. 23, 2001. To the extent that they are consistent herewith, the aforementioned applications are incorporated herein by reference.

FIELD OF THE INVENTION

The invention relates to water swellable or lubricious, antimicrobial and anti-inflammatory coatings for substrates such as medical devices, and methods of preparing same.

BACKGROUND OF THE INVENTION

To improve the lubricity of medical devices such as catheters, probes or feeding tubes which are inserted into a human or animal body cavity, coatings have been developed. Jelly-like coatings have been smeared onto the surface of medical devices before insertion into body cavities. However, such coatings are easily dislodged from the medical device, causing discomfort on removal. Furthermore, the jelly-like coatings can raise an additional risk of infection.

Another approach to reducing the coefficient of friction of medical devices has been to use oil, silicone or polymeric materials which are coated with such materials as Teflon®. These approaches provided limited lubricity, or introduced possible sources of infection.

Typical microorganisms involved in infection arising from the use of medical devices include *Staphylococcus epidermidis, Staphylococcus aureus, Pseudomonas aeruginosa, Escherichia coli* and *Proteus mirabilis,* fungi and yeast such as *Aspergillus fumigatus* and *Candida albicans.*

Numerous lubricious polymeric coatings are known for use on medical devices and other substrates. These coatings typically use a hydrophilic polymers which bind to the surface of the substrate and exhibit slipperiness (lubricity) on wetting. However, as a source for infection, these coatings can still be problematic.

There is still a need for an effective lubricious coating for substrates, which also provides antimicrobial protection.

SUMMARY OF THE INVENTION

The present invention provides water swellable, and most preferably lubricious, coatings useful for a wide variety of substrates. The coatings contain a water swellable, preferably lubricious, polymer, which provides lubricity on wetting, and a nanocrystalline antimicrobial powder formed with atomic disorder, which acts as both an antimicrobial agent and an anti-inflammatory agent, without interfering with the enhanced lubricity. It is particularly surprising and advantageous to discover that the inclusion of the atomically disordered antimicrobial metal component of the coatings of the present invention adheres well to the substrates and does not interfere with the lubricity properties of the final, dried coating. The antimicrobial metal component provides not only antimicrobial activity, but also anti-inflammatory activity, when wetted. It is also surprising that the coatings of the invention, which are formed from solutions of the polymer and the metal powder and then dried, continue to provide both antimicrobial and anti-inflammatory activity when rehydrated for actual use. The initial hydration of the polymer and metal powder to form the coating does not deactivate the metal powder. Importantly, the antimicrobial and anti-inflammatory activities are also found to be sustainable, that is not merely instantaneous, but continuing over an extended time period such as hours, days or weeks. Also important is the discovery that the coatings of the present invention provide a significant reduction to biofilm formation on the coated substrates.

Nanocrystalline powders of the antimicrobial metal, most preferably a noble metal, formed with atomic disorder can be prepared either as nanocrystalline coatings on powdered substrates such as chitin, or may be prepared as nanocrystalline coatings on a substrate such as a silicon wafer, and then scraped off as a nanocrystalline powder. In either case, the coatings are formed with atomic disorder using such techniques as physical vapour deposition or modified inert gas condensation as taught in prior patent applications WO 93/23092, published Nov. 25, 1993, and WO 95/13704, published May 26, 1995, both of which name Burrell et al., as inventors. Alternatively, to impart atomic disorder, a fine grained or nanocrystalline powder of the antimicrobial or noble metal may be cold worked to impart atomic disorder, as disclosed in prior patent application WO 93/23092. Still alternatively, the metal powders may be formed in accordance with the novel powder manufacturing process disclosed herein.

Broadly stated, the invention provides a method of coating a substrate comprising forming a liquid medium containing a water swellable polymer (preferably a lubricious polymer), a solvent and a powder of one or more antimicrobial metals formed with atomic disorder; and coating the substrate from the liquid medium to provide a gel coating that adheres to the substrate, and becomes antimicrobial and anti-inflammatory when wet.

In another broad aspect, the invention provides a substrate coated with a water swellable gel coating, comprising a substrate, and a water swellable gel coating adhering to the substrate, wherein the coating includes a water swellable polymer and one or more antimicrobial metals formed with atomic disorder, and wherein the gel coating becomes antimicrobial and anti-inflammatory when wet.

In yet another broad aspect, the invention provides a kit for coating a substrate comprising a water swellable polymer; a powder of one or more antimicrobial metals formed with atomic disorder; and optionally a solvent for the water swellable polymer.

The lubricious polymer is preferably a hydrophilic polymer in powder form, most preferably one or more of carboxymethyl cellulose, polyvinyl alcohol and alginate. The antimicrobial metal is preferably one or more of Ag, Au, Pd or Pt (most preferably Ag), in a nanocrystalline powder form (grain size less than 100 nm, more preferably less than 50 nm, more preferably less than 40 nm, and most preferably less than 25 nm), and with particulate size preferably less than 100 $\mu$m, more preferably less than 40 $\mu$m, and most preferably less than 10 $\mu$m).

The invention also broadly provides a method of forming a metal powder comprising sputtering a metal coating in a sputtering apparatus equipped to sputter onto a moving or rotating surface, and then scraping the coating off the moving or rotating surface with one or more scrapers to form a metal powder.

As used herein and in the claims, the terms and phrases set out below have the meanings which follow.

"Metal" or "metals" includes one or more metals whether in the form of substantially pure metals, alloys or compounds such as oxides, nitrides, borides, sulphides, halides or hydrides.

"Antimicrobial metals" are silver, gold, platinum, palladium, iridium, zinc, copper, tin, antimony, bismuth, or mixtures of these metals with same or other metals, silver, gold, platinum and palladium being preferred, and silver being most preferred.

"Noble metals" are silver, gold, platinum and palladium, or mixtures of such metals with same or other metals, with silver metal being the most preferred.

"Antimicrobial effect" means that atoms, ions, molecules or clusters of the antimicrobial or noble metal are released into the electrolyte which the coating contacts in concentration sufficient to inhibit microbial growth on and in the vicinity of the coating. The most common methods of measuring an antimicrobial effect are a zone of inhibition test (which indicates an inhibitory effect, whether microbiostatic or microbiocidal) or a logarithmic reduction test (which indicates a microbiocidal effect). In a zone of inhibition test (ZOI) the material to be tested is placed on a bacterial lawn (or a lawn of other microbial species) and incubated. A relatively small or no ZOI (ex. less than 1 mm) indicates a non-useful antimicrobial effect, while a larger ZOI (ex. greater than 5 mm) indicates a highly useful antimicrobial effect. The ZOI is generally reported as a corrected zone of inhibition (CZOI), wherein the size of the test sample is subtracted from the zone. A logarithmic reduction test in viable bacteria is a quantitative measure of the efficacy of an antibacterial treatment; for example, a 5 log reduction means a reduction in the number of microorganisms by 100,000-fold (e.g., if a product contained 100,000 pertinent microorganisms, a 5 log reduction would reduce the number of pertinent microorganisms to 1). Generally, a 3 log reduction represents a bactericidal effect. The logarithmic reduction test involves combining an inoculum of bacteria or other microbial species with the test treatment, incubating the inoculum with the test treatment, recovering the bacteria or other microbial species, and enumerating the bacteria or other microbial species using serial dilutions. Examples of these tests are set out in the examples which follow.

"Anti-inflammatory effect" means a reduction in one ore more of the symptoms of erythema (redness), edema (swelling), pain and pruritus which are characteristic of inflammatory conditions.

"Biocompatible" means generating no significant undesirable host response for the intended utility. Most preferably, biocompatible materials are non-toxic for the intended utility. Thus, for human utility, biocompatible is most preferably non-toxic to humans or human tissues.

"Sustained release" or "sustainable basis" are used to define release of atoms, molecules, ions or clusters of an antimicrobial or noble metal that continues over time measured in hours or days, and thus distinguishes release of such metal species from the bulk metal, which release such species at a rate and concentration which is too low to be therapeutically effective, and from highly soluble salts of antimicrobial or noble metals such as silver nitrate, which releases silver ions virtually instantly, but not continuously, in contact with an alcohol or electrolyte.

"Atomic disorder" includes high concentrations of one or more of: point defects in a crystal lattice, vacancies, line defects such as dislocations, interstitial atoms, amorphous regions, grain and sub grain boundaries and the like relative to its normal ordered crystalline state. Atomic disorder leads to irregularities in surface topography and inhomogeneities in the structure on a nanometer scale.

"Normal ordered crystalline state" means the crystallinity normally found in bulk metal materials, alloys or compounds formed as cast, wrought or plated metal products. Such materials contain only low concentrations of such atomic defects as vacancies, grain boundaries and dislocations.

"Diffusion", when used to describe conditions which limit diffusion in processes to create and retain atomic disorder, i.e., which freeze-in atomic disorder, means diffusion of atoms (adatom diffusion) and/or molecules on the surface or in the matrix of the material being formed.

"Alcohol or water-based electrolyte" is meant to include any alcohol or water-based electrolyte that the antimicrobial materials of the present invention might contact in order to activate (i.e., cause the release of species of the antimicrobial metal) into same. The term is meant to include alcohols (generally short chain $C_6$ or less), water, gels, fluids, solvents, and tissues containing, secreting or exuding water, or water-based electrolytes, including body fluids (for example blood, urine or saliva), and body tissue (for example skin, muscle or bone).

"Bioabsorbable" as used herein in association includes substrates which are useful in medical devices, that is which are biocompatible, and which are capable of bioabsorption in period of time ranging from hours to years, depending on the particular application.

"Bioabsorption" means the disappearance of materials from their initial application site in the body (human or mammalian) with or without degradation of the dispersed polymer molecules.

"Cold working" as used herein indicates that the material has been mechanically worked such as by milling, grinding, hammering, mortar and pestle or compressing, at temperatures lower than the recrystallization temperature of the material. This ensures that atomic disorder imparted through working is retained in the material.

"Pharmaceutically- or therapeutically-acceptable" is used herein to denote a substance which does not significantly interfere with the effectiveness or the biological activity of the active ingredients (antimicrobial and anti-inflammatory activities) and which is not toxic or has an acceptable toxic profile to the host to which it is administered or contacted.

"Therapeutically effective amount" is used herein to denote any amount of the nanocrystalline antimicrobial or noble metals which will exhibit an anti-microbial and an anti-inflammatory effect in use. The amount of the active ingredient, that is the antimicrobial or noble metal in the form of a coating, powder or dissolved in liquid solution, will vary with the substrate being coated, and the time which the substrate is to remain in contact with biological fluids and the like. Appropriate amounts in any given instance will be readily apparent to those skilled in the art or capable of determination by routine experimentation.

"Nanocrystalline" is used herein to denote single-phase or multi-phase polycrystals, the grain size of which is less than about 100, more preferably <50, even more preferably <40, even more preferably <30, and most preferably <25 nanometers in at least one dimension. The term, as applied to the crystallite or grain size in the crystal lattice of coatings, powders or flakes of the antimicrobial or noble metals, is not meant to restrict the particle size of the materials when used in a powder form.

"Powder" is used herein to include particulates of the nanocrystalline antimicrobial or noble metals ranging from nanocrystalline sized powders to flakes. Preferably, powders of the antimicrobial or noble metals used in the present invention are sized at less than 100 $\mu$m, and more preferably less than 40 $\mu$m, and most preferably less than 10 $\mu$m.

"Grain size", or "crystallite size" means the size of the largest dimension of the crystals in the antimicrobial or noble metal coating or powder.

"Lubricous polymers" are polymers which become lubricious on wetting with water or a water or alcohol-based electrolyte. Most lubricious polymers are hydrophilic, by some hydrophobic polymers may also function as lubricious polymers if they have a sufficient degree of lubricity on wetting.

"Hydrophilic" means that water droplets do not readily form beads on the surface of such hydrophilic material, but instead, the water droplets tend to assume a contact angle of less than 45 degrees and readily spread on its surface. The term "hydrophilic polymer" is meant to include polymers which are hydrophilic on wetting, and which also produce a lubricity in that wetted state. "Hydrophilic polymer" is also meant to include "water swellable" polymers, wherein "water swellable" means a substantially hydrophilic polymer which, even though not soluble in water, absorbs sufficient water to render it lubricious in the hydrated state. While these definitions all refer to water as an agent for hydration, it should be understood to include other water or alcohol-based electrolytes including bodily fluids which are capable of hydrating or swelling the polymer.

"Solvent" is the term used herein to describe the liquid medium used to solubilize, disperse or suspend the components of the coatings of the present invention prior to applying the coating to the substrate. As used herein, the term does not imply that the components of the coatings are completely dissolved in the solvent, it is sufficient that the polymer is approximately 1 wt % soluble in the solvent, more preferably at least 2 wt % soluble in the solvent, or is otherwise effective in promoting some swelling of the polymer.

When used herein and in the claims, the term "nanocrystalline antimicrobial metal" and similar terminology such as "nanocrystalline coatings or powders" is meant to refer to antimicrobial metals formed with atomic disorder and having nanocrystalline grain size.

When used herein and in the claims the term "kit" is meant to refer to a package or container with ingredients for a coating of the present invention or containing a coated substrate, whether the ingredients are in separate phases or containers, or mixed together.

DESCRIPTION OF THE PREFERRED EMBODIMENTS

The lubricious gel coatings of the present invention are prepared by mixing one or more suitable lubricious polymers with the atomically disordered antimicrobial or noble metals in a suitable solvent, and then using this mixture to coat the substrate. The solvent does not need to dissolve the individual components, but rather is suitable provided it can provide the two components in a suspension which at least partially hydrates the polymer, and does not interfere with the end activity of any of the components. The individual components of the lubricious coating may be provided in kit form such that the mixture and coating are prepared by the end user close to the time of use, or the kit may include the coating components in a pre-mixed form.

The solvent is one suitable for suspending the components of the coatings without interfering with the antimicrobial, anti-inflammatory activities or the desired biocompatible and lubricious properties of the final coating. Exemplary solvents include esters, toluene, lactones, dimethylformamide, halogenated solvents, tetrahydrofuran, dioxane, alkyl acetates, acetonitrile, butyrolactone, ethyl acetate, chloroform, methanol, ethanol, propanol, DMSO (dimethyl sulfoxide) and mixtures thereof.

Preferred solvents are water (preferably nanopure), and alcohols such as methanol, ethanol and propanol, and DMSO, with water being most preferred.

The substrate may be formed of virtually any material, including polyurethane, polyvinylchloride, other vinyl polymers, polycarbonate, polystyrene, nylon, polyesters and polyacrylates, polypropylene, polybutylene, tetrafluoroethylene, polyvinylacetal, elastomers, latex rubber, rubber, silicone, other plastic, metal, glass, and composites.

The substrate to be coated is any medical device or other substrate which will benefit from the provision of a lubricious coating, whether implantable, percutaneous, transcutaneous or surface applied. Particular substrates which may be coated include catheters (including urinary, in-dwelling, drainage catheters, etc.), bone screws, total joints, vascular grafts, soft tissue repair implants such as hernia meshes, guide wires, needles, wound drains, pacemaker leads, condoms, contact lenses, peristaltic pump chambers, arteriovenous shunts, gastroenteric feed tubes, endotracheal tubes, gloves and implants. Additional substrates which can be coated include venous catheters, arterial catheters, central line and peripheral line catheters, halo screws, cannulas, endoscopes, laparoscopes, sutures, staples, myringotomy tubes, nasal packings, dressings and gauze.

The lubricious polymers suitable for use in accordance with the present invention are water-soluble or water-swellable polymers which are substantially more lubricious when wetted with water, or with a water or alcohol-based electrolyte, than when dry. Such polymers are well known in the art. Preferred are hydrophilic polymers, including sodium, potassium and calcium alginates, carboxymethylcellulose, agar, gelatin, polyvinyl alcohol, collagen, pectin, chitin, chitosan, poly (α-amino acids), polyester, poly-1-caprolactone, polyvinylpyrrolidone, polyethylene oxide, polyvinyl alcohol, polyether, polysaccharide, hydrophilic polyurethane, polyhydroxyacrylate, polymethacrylate, dextran, xanthan, hydroxypropyl cellulose, methyl cellulose, and homopolymers and copolymers of N-vinylpyrrolidone, N-vinyllactam, N-vinyl butyrolactam, N-vinyl caprolactam, other vinyl compounds having polar pendant groups, acrylate and methacrylate having hydrophilic esterifying groups, hydroxyacrylate, and acrylic acid, and combinations thereof.

Most preferred lubricious polymers include hydrocolloid powders such as sodium, potassium and calcium alginates, polyvinyl alcohol, and carboxymethylcellulose. Other preferred lubricious polymers are cellulose and derivatives thereof, starch, glycogen, gelatin, pectin, chitosan, chitin, collagen, gum arabic, locust bean gum, karaya gum, gum tragacanth, ghatti gum, agar—agar, carrageenans, alginates, carob gum, guar gum, xanthan gum, poly (α-amino acids), polyester and poly-1-caprolactone.

The lubricious polymers may be physically stabilized by cross-linking, as is known in the art.

The lubricious coatings of the present invention are prepared from a liquid medium which contains a solvent capable of forming a solution, dispersion, suspension or emulsion of the polymer and metal components of the coating. In this form, the liquid medium has a gel-like consistency, and can be used in this form in some applications, such as gloves.

The coatings can then be readily applied to a substrate by dipping, spraying, knife coating, roller coating, smearing or the like. Dipping is particularly preferred. The substrate should be thoroughly cleaned to remove surface impurities which could interfere with adhesion. It is recommended that various plastic or polymeric substrates be treated with oxidizing solutions prior to the coating application. For instance, natural rubber can be treated with a sodium chlorate solution.

The process of applying the coating to the substrate is preferably conducted at atmospheric pressure and at temperatures between about 0 and 50° C., more preferably between about 10 and 40° C. For some applications, the wet coated substrate can be used in that state, while in other applications, the coating is preferably dried at a temperature below the recrystallization temperature of the antimicrobial or noble metal (i.e., at a temperature below that which would anneal out the atomic disorder). The coating is dried at −80 to 50° C., more preferably between 10 and 40° C. Most preferably, the coating is air dried at room temperature.

The concentration of the polymers in the liquid medium is sufficient to provide the desired amount of lubricity in the final coating. Typically, the concentration of the polymers will range from about 0.1 to 10 wt %, more preferably 0.5 to 5 wt %. The concentration of the antimicrobial or noble metal is sufficient to provide the desired antimicrobial and anti-inflammatory activities in the final coating. Typically the concentration will range from about 0.001 to 30 wt %, more preferably 0.1 to 5 wt %.

Hydrating agents may be added. Binders for improved adhesion to the substrate may be included. The binder may be applied to the substrate simultaneously or prior to the coating.

Other agents which are known and which might be included are preservatives such as methyl paraben and propyl paraben, texturizing agents, thickeners, anticoagulants such as heparin, β-glucan, hormones, hyaluronic acid, cytokines such as epidermal growth factor, platelet derived growth factor, transforming growth factor and interleukins, and bone morphogenetic proteins, and the like. Polyvinyl alcohol is a particularly preferred polymer and also acts as a texturizing agent, methyl or propyl parabens are particularly preferred preservatives. These other agents may be included in amounts in the range of 0.1 to 5 wt %, or any therapeutically acceptable amount.

All agents, solvents and components used in the coatings of the present invention must be non-toxic and physiologically acceptable for the intended purpose, and must not substantially interfere with the activity of the coating so as to deleteriously affect the lubricity, the antimicrobial effect or the anti-inflammatory activity. Ingredients are thus only included in therapeutically or pharmaceutically acceptable amounts. Ingredients to be avoided or limited in the coatings of the present invention, preferably to less than 0.01 wt %, are glycerin, glycerols, chloride salts, aldehydes, ketones, long chain alcohols, and triethanolamine.

The substrate coated with the lubricious gel coatings of the present invention may be used in their initial wetted state, but are more preferably dried and then rehydrated in use.

Powders of Atomically Disordered Antimicrobial or Noble Metals

Crystalline powder forms of the antimicrobial or noble metals (particularly preferred being Ag, Au, Pt, and Pd) can be prepared as free standing powders, by coating powdered substrates, or from coatings on substrates which are then collected, for example by scraping, and then sized. The powders may be prepared as pure metals, metal alloys or compounds such as metal oxides or metal salts, by vapour deposition, mechanical working, or compressing to impart the atomic disorder. The crystalline powders are formed with atomic disorder in accordance with the techniques published in the prior patent applications of Burrell et al., see for example WO 93/23092, published Nov. 25, 1993, and WO 95/13704, published May 26, 1995. The atomic disorder will most typically be formed in the metal powders during physical vapour deposition as set out below or by mechanically imparting the disorder, such as by milling, grinding, hammering, mortar and pestle or compressing, under conditions of low temperature (i.e., temperatures less than the temperature of recrystallization of the material) to ensure that annealing or recyrstallization does not take place.

Alternatively, the powders may be formed by inert-gas condensation techniques, which are modified to provide atomic disorder in the powder produced, as taught in WO 95/13704 to Burrell et al.

Powders of the antimicrobial or noble metals are preferably formed by physical vapour deposition (PVD) onto a substrate such as a cold finger, a silicon wafer, solid plates, a rotating cylinder, a continuous belt in a roll coater, or on steel collectors in known PVD coaters. Preparation of powders of the present invention by sputtering onto a continuous belt in a roll coater, or other some other moving or rotating substrate surface is particularly advantageous, inasmuch as it can quickly and easily yield a relatively large supply of free-standing powder at a relatively low cost. A stainless steel belt can be used in the roll coating process without the need to provide additional cooling of the substrate. The powders or coatings and then are then scraped off to form a powder, and may be sized to avoid overly large particulates. The powders are scraped off the moving surface with scrapers which contact the moving surface at an angle sufficient to remove the coating in flake or powder form. The coating may be scraped off with scrapers angled for forward cutting of the coating from the moving surface, or with scrapers which remove the coating from the moving surface by reverse dragging action on the surface. The scrapers may be suspended above the belt, and either weighted or spring loaded to apply pressure sufficient to remove the coating from the moving surface. With a continuous belt, the scrapers can conveniently be located above the end rollers to remove the coating with a reverse dragging action as the belt rounds the end roller.

Alternatively, the powders of the antimicrobial or noble metals may be formed on powdered substrates which are biocompatible, or otherwise compatible for the end use of the lubricious coating. Particularly preferred powdered substrates are hydrocolloids, particularly those which are bioabsorbable and/or hygroscopic powders such as chitin. Exemplary bioabsorbable and/or hygroscopic powders are composed of:

Synthetic Bioabsorbable Polymers: for example polyesters/polyactones such as polymers of polyglycolic acid, glycolide, lactic acid, lactide, dioxanone, trimethylene carbonate etc., polyanhydrides, polyesteramides, polyortheoesters, polyphosphazenes, and copolymers of these and related polymers or monomers.

Naturally Derived Polymers:
Proteins: albumin, fibrin, collagen, elastin;
Polysaccharides: chitosan, alginates, hyaluronic acid; and
Biosynthetic Polyesters: 3-hydroxybutyrate polymers.

The preferred conditions which are used to create atomic disorder during a physical vapour deposition process include:

a low substrate temperature, that is maintaining the surface to be coated at a temperature such that the ratio of the substrate temperature to the melting point of the metal (in degrees Kelvin) is less than about 0.5, more preferably less than about 0.35 and most preferably less than about 0.3; and optionally one or both of:

a higher than normal working gas pressure (or in cases where there is no working gas, the ambient gas pressure) i.e., for vacuum evaporation: e-beam or arc evaporation, greater than 0.001 Pa (0.01 mT), gas scattering evaporation (pressure plating) or reactive arc evaporation, greater than 2.67 Pa (20 mT); for sputtering: greater than 10 Pa (75 mT); for magnetron sputtering: greater than about 1.33 Pa (10 mT); and for ion plating: greater than about 26.67 Pa (200 mT); and maintaining the angle of incidence of the coating flux on the surface to be coated at less than about 75°, and preferably less than about 30°.

The therapeutic effects of the material so produced is achieved when the lubricous coating is brought into contact with an alcohol or a water-based electrolyte, thus releasing metal ions, atoms, molecules or clusters. The concentration of the metal species which is needed to produce a therapeutic effect will vary from metal to metal.

The ability to achieve release of metal atoms, ions, molecules or clusters on a sustainable basis from a metal powder component is dictated by a number of factors, including PVD coating characteristics such as composition, structure, solubility and thickness, and the nature of the environment in which the device is used. As the level of atomic disorder is increased, the amount of metal species released per unit time increases. For instance, a silver metal film deposited by magnetron sputtering at $T/T_m<0.5$ and a working gas pressure of about 0.93 Pa (7 mT) releases approximately ⅓ of the silver ions that a film deposited under similar conditions, but at 4 Pa (30 mT), will release over 10 days. Films that are created with an intermediate structure (ex. lower pressure, lower angle of incidence etc.) have Ag release values intermediate to these values as determined by bioassays. This then provides a method for producing controlled release metallic PVD coatings. Slow release PVD coatings are prepared such that the degree of disorder is low while fast release PVD coatings are prepared such that the degree of disorder is high.

For continuous, uniform PVD coatings, the time required for total dissolution will be a function of film thickness and the nature of the environment to which they are exposed. The relationship in respect of thickness is approximately linear, i.e. a two fold increase in film thickness will result in about a two-fold increase in longevity.

It is also possible to control the metal release from a PVD coating by forming a thin film coating with a modulated structure. For instance, a coating deposited by magnetron sputtering such that the working gas pressure was low (ex. 2 Pa or 15 mT) for 50% of the deposition time and high (ex. 4 Pa or 30 mTorr) for the remaining time, has a rapid initial release of metal ions, followed by a longer period of slow release. This type of PVD coating is extremely effective for devices such as urinary catheters for which an initial rapid release is required to achieve immediate anti-microbial concentrations followed by a lower release rate to sustain the concentration of metal ions over a period of weeks.

The substrate temperature used during vapour deposition should not be so low that annealing or recrystallization of the PVD coating takes place as the coating warms to ambient temperatures or the temperatures at which it is to be used (ex. body temperature). This allowable $\Delta T$, that the temperature differential between the substrate temperature during deposition and the ultimate temperature of use, will vary from metal to metal. For the most preferred metal, Ag, preferred substrate temperatures of −20 to 200° C., more preferably −10° C. to 100° C. are used.

Atomic order may also be achieved by preparing composite metal materials, that is materials which contain one or more antimicrobial or noble metals in a metal matrix which includes atoms or molecules different from the antimicrobial or noble metals.

The preferred technique for preparing a composite material is to co- or sequentially deposit the antimicrobial or noble metal(s) with one or more other inert, biocompatible metals selected from Ta, Ti, Nb, Zn, V, Hf, Mo, Si, Al and alloys of these metals or other metal elements, typically other transition metals. Such inert metals have a different atomic radii from that of the antimicrobial or noble metals, which results in atomic disorder during deposition. Alloys of this kind can also serve to reduce atomic diffusion and thus stabilize the disordered structure. Thin film deposition equipment with multiple targets for the placement of each of the antimicrobial or noble and biocompatible metals is preferably utilized. When layers are sequentially deposited the layer(s) of the biocompatible metal(s) should be discontinuous, for example as islands within the antimicrobial or noble metal matrix. The final weight ratio of the antimicrobial or noble metal(s) to biocompatible metal(s) should be greater than about 0.2. The most preferable biocompatible metals are Ti, Ta, Zn and Nb. It is also possible to form the anti-microbial coating from oxides, carbides, nitrides, sulphides, borides, halides or hydrides of one or more of the antimicrobial or noble metals and/or one or more of the biocompatible metals to achieve the desired atomic disorder.

Another composite material may be formed by reactively co- or sequentially depositing, by physical vapour techniques, a reacted material into the thin film of the antimicrobial or noble metal(s). The reacted material is an oxide, nitride, carbide, boride, sulphide, hydride or halide of the antimicrobial or noble and/or biocompatible metal, formed in situ by injecting the appropriate reactants, or gases containing same, (ex. air, oxygen, water, nitrogen, hydrogen, boron, sulphur, halogens) into the deposition chamber. Atoms or molecules of these gases may also become absorbed or trapped in the metal film to create atomic disorder. The reactant may be continuously supplied during deposition for codeposition or it may be pulsed to provide for sequential deposition. The final weight ratio of reaction product to antimicrobial or noble metal(s) should be greater than about 0.05. Air, oxygen, nitrogen and hydrogen are particularly preferred reactants, with oxygen being most preferred.

The above deposition techniques to prepare composite PVD coatings may be used with or without the conditions of lower substrate temperatures, high working gas pressures and low angles of incidence previously discussed. One or more of these conditions are preferred to retain and enhance the amount of atomic disorder created in the coating.

Most preferably, powders of the present invention are sized at less than 100 μm, and more preferably less than 40 μm, and most preferably about 3–5 μm in size to avoid being abrasive in the coating.

The antimicrobial and anti-inflammatory effects of the nanocrystalline powder is achieved when the lubricous coating, and thus the powder, is brought into contact with an alcohol or a water-based electrolyte, thus releasing the antimicrobial or noble metal ions, atoms, molecules or clusters.

Sterilization and Packaging

Powders of the antimicrobial or noble metal formed with atomic disorder or the substrates formed with the lubricious coatings of this invention are preferably sterilized without applying excessive thermal energy, which can anneal out the atomic disorder, thereby reducing or eliminating a useful release of antimicrobial or noble metal species. Gamma radiation is preferred for sterilizing such dressings, as discussed in WO 95/13704. Electron beam and ethylene oxide sterilization techniques can also be used.

The sterilized coating materials, or the coated substrates should be sealed in packaging, containers or kits which limit moisture and light penetration to avoid additional oxidation or reduction of the antimicrobial metal. Polyester peelable pouches are exemplary.

The following examples are presented for illustrative purposes and are not intended to limit the scope of the claims which follow.

EXAMPLE 1

Preparation of Atomic Disordered Nanocrystalline Silver Powders

Nanocrystalline silver coatings were prepared by sputtering silver in an oxygen-containing atmosphere directly onto an endless stainless steel belt of a magnetron sputtering roll coater, or onto silicon wafers on the belt. The belt did not need to be cooled. The coatings were scraped off with the belt with suspended and weighted metal scrapers which dragged along the coating in a reverse direction as the belt rounded the end rollers. For the coated silicon wafers, the coatings were scraped off with a knife edge. The sputtering conditions were as follows:

TABLE 1

| Sputtering Conditions | |
|---|---|
| Target: | 99.99% Ag |
| Target Size(individual, 23 targets): | 15.24 cm × 1216.125 cm |
| Working Gas: | 75:25 wt % Ar/$O_2$ |
| Working Gas Pressure: | 5.33 Pa (40 mTorr) |
| Total Current: | 40 A |
| Base Pressure: | $5.0 \times 10^{-5}$ Torr (range: $1 \times 10^{-4} - 9 \times 10^{-7}$ Torr or $1 \times 10^{-2} - 1.2 \times 10^{-4}$ Pa) |
| Sandvik Belt Speed: | 340 mm/min |
| Voltage: | 370 V |

Note
pressure conversions to Pa herein may not be accurate, the most accurate numbers are in Torr and mTorr (mT) units.

The powder had a particle size ranging from 2 $\mu$m to 100 $\mu$m, with grain or crystallite size of 8 to 10 nm (i.e., nanocrystalline), and demonstrated a positive rest potential.

Similar atomic disordered nanocrystalline silver powders were formed as set forth hereinabove by magnetron sputtering onto cooled steel collectors, under conditions taught in the prior Burrell et al. patents to produce atomic disorder.

EXAMPLE 2

Lubricious Gel Coating

A gel was made using carboxymethyl cellulose (2%), polyvinyl alcohol (0.5%), methyl paraben (0.1%), propyl paraben (0.02%), nanocrystalline silver powder of Example 1 (0.1%) and water (all amounts in weight percentages). After mixing the gel well, to distribute the nanocrystalline silver powder, segments (2 cm) of latex foley catheters (14 French) were dipped coated and allowed to dry at room temperature for 24 h. The segments were then tested for antimicrobial effect, using a corrected zone of inhibition technique, against *Pseudomonas aeruginosa* and *Staphylococcus aureus*. The corrected zone of inhibition method involved growing a culture of the bacterium of interest in Tryptic Soy Broth for 16 hours at 37° C. These cultures were then used to inoculate a second test tube of Tryptic Soy Broth, which was grown up to the density of a 0.5 McFarland standard. A 0.1 ml volume of this inoculant is then placed on a Mueller-Hinton agar surface in a standard Petri dish where it was spread to form a uniform lawn. The coated catheter segment was then placed on the surface of the bacterial lawn and the Petri plate and contents were incubated at 37° C. for 24 hours. After 24 hours the zone of inhibition (if any) were measured in millimeters (mm) and corrected by the size of the contact area between the catheter and the agar surface. This formulation generated corrected zones of inhibition with *P. aeruginosa* and *S. aureus* of 5 and 7 mm respectively.

EXAMPLE 3

Lubricious Gel Coating

A gel was made using carboxymethyl cellulose (2%), nanocrystalline silver powder of Example 1 (0.1%) and water. After mixing the gel well, to distribute the nanocrystalline silver powder, segments (2 cm) of latex foley catheters (14 French) were dipped coated and allowed to dry at room temperature for 24 h. The segments were then tested for antimicrobial efficacy, using a corrected zone of inhibition technique, against *Pseudomonas aeruginosa* and *Staphylococcus aureus*. The corrected zone of inhibition method involved growing a culture of the bacterium of interest in Tryptic Soy Broth for 16 hours at 37° C. These cultures were then used to inoculate a second test tube of Tryptic Soy Broth, which was grown up to the density of a 0.5 McFarland standard. A 0.1 ml volume of this inoculant was then placed on a Mueller-Hinton agar surface in a standard Petri dish where it was spread to form a uniform lawn. The coated catheter segment was then placed on the surface of the bacterial lawn and the Petri plate and contents were incubated at 37° C. for 24 hours. After 24 hours the zone of inhibition (if any) was measured in millimeters (mm) and corrected by the size of the contact area between the catheter and the agar surface. This formulation generated corrected zones of inhibition with *P. aeruginosa* and *S. aureus* of 8 and 6 mm respectively.

EXAMPLE 4

Lubricious Gel Coating

A gel was made using sodium alginate (2%), nanocrystalline silver powder of Example 1 (0.1%) and water. After mixing the gel well, to distribute the nanocrystalline silver powder, segments (2 cm) of latex foley catheters (14 French) were dipped coated and allowed to dry at room temperature for 24 h. The segments were then tested for antimicrobial efficacy, using a corrected zone of inhibition technique, against *Pseudomonas aeruginosa* and *Staphylococcus aureus*. The corrected zone of inhibition method involved growing a culture of the bacterium of interest in Tryptic Soy Broth for 16 hours at 37° C. These cultures were then used to inoculate a second test tube of Tryptic Soy Broth, which is grown up to the density of a 0.2 McFarland standard. A 0.1 ml volume of this inoculant was then placed on a Mueller-Hinton agar surface in a standard Petri dish where it was spread to form a uniform lawn. The coated catheter segment was then placed on the surface of the bacterial lawn and the Petri plate and contents were incubated at 37° C. for 24 hours. After 24 hours the zone of inhibition (if any) was measured in millimeters (mm) and corrected by the size of the contact area between the catheter and the agar surface. This formulation generated corrected zones of inhibition with P. aeruginosa and S. aureus of 5 and 5 mm respectively.

EXAMPLE 5

Lubricity Test

Five Bard latex urinary catheters were coated with a CMC-Ag gel using a method as described in Example 3 and another five catheters were coated an alginate —Ag gel using a method as described in Example 4. The coated catheters were tested for lubricity with five uncoated latex catheters as controls.

Prior to testing, all catheters were wet by dipping in nanopure water. All catheters felt slippery to the touch. The catheters were placed in a curved glass tube with upper end connected to an Instron mechanic testing unit and a 10 gram weight hung on the lower end. During testing, the Instron pulls the catheter upward. The force applied to pull the catheter through the glass tube reflects the friction between catheter surface and inner surface of the glass tube. A load curve against time was recorded in each test and an average load to pull the catheter through the glass tube was calculated. The data of the average loads (lb/kg) are a presented in Table 2 and each datum point represents a mean of five tests.

TABLE 2

| Samples | Average Load (lb/kg) |
| --- | --- |
| Uncoated Control Catheters | 0.165 ± 0.020 lb/0.075 kg |
| CMC Gel Coated Catheters | 0.062 ± 0.005 lb/0.028 kg |
| Alginate Gel Coated Catheters | 0.076 ± 0.028 lb/0.035 kg |

The results showed that both CMC and alginate gel coatings reduced average forces (loads) that were required to pull the catheters up to less than half of that for uncoated control catheters. This suggested that both coatings significantly increased lubricity of catheter surfaces.

EXAMPLE 6

Other Lubricious Gel Coatings

No. 1—A commercial carboxymethyl cellulose/pectin gel (Duoderm®, Convatec) was combined with nanocrystalline silver powder prepared as set forth in Example 1 to produce a gel with 0.1% silver. A logarithmic reduction test was performed as follows in the gel using *Pseudomonas aeruginosa*. The inoculum was prepared by placing 1 bacteriologic loopful of the organism in 5 ml of trypticase soy broth and incubating it for 3–4 h. The inoculum (0.1 ml) was then added to 0.1 ml of gel and vortexed (triplicate samples). The mixture was incubated for one-half hour. Then 1.8 ml of sodium thioglycollate-saline (STS) solution was added to the test tube and vortexed. Serial dilutions were prepared on $10^{-1}$ to $10^{-7}$. A 0.1 mL aliquot of each dilution was plated in duplicate into Petri plates containing Mueller-Hinton agar. The plates were incubated for 48 h and then colonies were counted. Surviving members of organisms were determined and the logarithmic reduction compared to the initial inoculum was calculated. The logarithmic reduction for this mixture was 6.2, indicating a significant bactericidal effect.

No. 2—Carboxymethyl cellulose (CMC) fibers were coated directly to produce an atomic disordered nanocrystalline silver coating, using magnetron sputtering conditions similar to those set forth in Example 1. The CMC was then gelled in water by adding 2.9 g to 100 mL volume. This material was tested using the method of No. 1. The material generated a 5.2 logarithmic reduction of *Pseudomonas aeruginosa*, demonstrating that the gel had a significant bactericidal effect.

No. 3—An alginate fibrous substrate was directly coated with an atomic disordered nanocrystalline silver coating using magnetron sputtering conditions similar to those set forth in Example 1. The alginate (5.7 g) was added to 100 mL volume of water to create a gel. This material was tested using the method of No. 1. The material generated a 5.2 logarithmic reduction of *Pseudomonas aeruginosa*, demonstrating that the gel had a significant bactericidal effect.

No. 4—A commercial gel containing CMC and alginate (Purilin gel, Coloplast) was mixed with a atomic disordered nanocrystalline silver powder to give a product with 0.1% silver. This was tested as above with both *Pseudomonas aeruginosa* and *Staphylococcus aureus*. Zone of inhibition data was also generated for this gel as follows. An inoculum (*Pseudomonas aeruginosa* and *Staphylococcus aureus*) was prepared as in No. 1 and 0.1 mL of this was spread onto the surface of Mueller-Hinton agar in a Petri dish. A six mm hole was then cut into the agar at the center of the Petri dish and removed. The well was filled with either 0.1 mL of the silver containing gel, a mupirocin containing cream or a mupirocin containing ointment. The Petri plates were then incubated for 24 h and the diameter of the zone of inhibition was measured and recorded.

The silver containing gel produced 9 mm zone of inhibition against both *Pseudomonas aeruginosa* and *Staphylococcus aureus*, while the mupirocin cream and ointment produced 42 and 48 mm zones against *Staphylococcus aureus* and 0 mm zones against *Pseudomonas aeruginosa*.

The silver containing gel reduced the *Pseudomonas aeruginosa* and *Staphylococcus aureus* properties by 4.4 and 0.6 log reductions, respectively, showing good bactericidal activity. The mupirocin cream and ointment generated 0.4 and 0.8, and 0.8 and 1.6, log reductions against *Staphylococcus aureus* and *Pseudomonas aeruginosa*, respectively. The silver gel had both a greater bactericidal effect and spectrum of activity than the mupirocin containing products.

Nos. 5–10—The formula for Nos. 5–10 are summarized in Table 3. Zones of inhibitions were determined as in No. 4 and log reductions were determined as in No. 1.

All formulae provided a broader spectrum of activity and a greater bactericidal effect than did mupirocin in a cream or ointment form. The mupirocin cream produced zones of inhibition of 42 and 0, and log reduction of 0.4 and 0.8, against *Staphylococcus aureus* and *Pseudomonas aeruginosa*, respectively.

TABLE 3

| # | CMC | PVA | Silver Powder | β-glucan | Methyl Paraben | Propyl Paraben | CZOI S. aureus | CZOI P. aeruginosa | Log Red'n S. aureus | Log Red'n P. aeruginosa |
|---|---|---|---|---|---|---|---|---|---|---|
| 5 | 2% | | 0.1% | | | | 11 | 13 | 1.4 | >6 |
| 6 | 2% | 0.5% | 0.1% | | 0.1 | 0.02 | 14 | 15 | 3.3 | >6 |
| 7 | 2% | 0.5% | 0.1% | | | | 13 | 14 | 2.0 | N/A |
| 8 | 2% | 0.5% | 0.1% | | 0.1 | | 14 | 14 | 2.0 | N/A |
| 9 | 2% | 0.5% | 0.1% | | | 0.20 | 14 | 14 | 2.0 | N/A |
| 10 | 2% | 0.5% | 0.1% | 0.5 | 0.1 | 0.20 | 14 | 14 | 2.0 | >6 |

No. 11—A commercially available gel (glyceryl polymethacrylate) was blended with Silver powder to produce a gel with a silver content of 0.1%. This gel was tested as in Nos. 5–10 and was found to produce zones of 15 mm against both *Staphylococcus aureus* and *Pseudomonas aeruginosa*. Log reductions of 1.7 and >5 were produced against *Staphylococcus aureus* and *Pseudomonas aeruginosa*. This gel product had a greater spectrum of activity than did mupirocin cream or ointment.

The silver gel solutions of No. 1–11 can be applied to substrates by hydrating and comminuting the coated substrate where needed and then drying the gel solution onto substrates to provide lubricious coatings of the present invention. The silver gels also have an anti-inflammatory effect, with reduction of edema and erythema symptoms.

No. 12—A gel coat for a urinary catheter was prepared using the formula in No. 6. The coating was applied to the catheter using a dipping method. The coating was air dried overnight. The dried gel coat was smooth and easy to handle. It was not tacky to touch and had excellent abrasion and adhesion properties. Upon rewetting, the surface became extremely slippery indicating excellent lubricious properties. A zone of inhibition test was performed against *Pseudomonas aeruginosa* using an inoculum as prepared in No. 1. The inoculum (0.1 mL) was spread over the surface of Mueller-Hinton agar in a Petri plate. The catheter was cut into 1" segments which were laid on their side into the middle of the Petri plate. Petri plates were incubated for 24 h and then the zone of inhibitions was measured. In all cases, zones of inhibition were generated that ranged from 7–10 mm. This indicates that wetting, drying and rehydrating had no negative effect on the antimicrobial activity of the gel coat.

Selected lubricious gels from the above examples were tested on both human and pig skin for an anti-inflammatory effect, and were found to reduce both erythema and oedemaa effects, indicating that the coatings of the present invention have a therapeutic effect which is both antimicrobial and anti-inflammatory.

All publications mentioned in this specification are indicative of the level of skill of those skilled in the art to which this invention pertains. All publications are herein incorporated by reference to the same extent as if each individual publication was specifically and individually indicated to be incorporated by reference.

The terms and expressions in this specification are, unless otherwise specifically defined herein, used as terms of description and not of limitation. There is no intention, in using such terms and expressions, of excluding equivalents of the features illustrated and described, it being recognized that the scope of the invention is defined and limited only by the claims which follow.

We claim:

1. A method of forming antimicrobial metal powder formed with atomic disorder comprising:

sputtering a metal coating in a sputtering apparatus equipped to sputter onto a moving or rotating surface, wherein (i) the moving or rotating surface is a continuous belt or rotating cylinder, and (ii) said surface is maintained at a temperature so that the ratio of the surface temperature to the melting point of the metal in degrees Kelvin is less than about 0.5; and scraping the coating off the moving or rotating surface with one or more scrapers to form said antimicrobial powder, wherein said one or more scrapers are suspended to contact the coating at an angle sufficient to remove the coating from the belt or cylinder.

2. The method as set forth in claim 1, wherein the belt is a metal belt in a magnetron sputtering roll coater.

3. The method as set forth in claim 2, wherein the metal is one or more antimicrobial metals.

4. The method as set forth in claim 3, wherein the antimicrobial metal is one or more of Ag, Au, Pd or Pt, and wherein the sputtering is conducted in an oxygen-containing atmosphere under conditions to form and retain atomic disorder in a nanocrystalline powder of the antimicrobial metal.

* * * * *